(12) United States Patent
Gaisch

(10) Patent No.: US 11,180,401 B2
(45) Date of Patent: Nov. 23, 2021

(54) PROCESS FOR THE TREATMENT OF WASTEWATER FORMED DURING THE PRODUCTION OF MODIFIED STARCHES

(71) Applicant: Franz Gaisch, Ottensheim (AT)

(72) Inventor: Franz Gaisch, Ottensheim (AT)

( * ) Notice: Subject to any disclaimer, the term of this patent is extended or adjusted under 35 U.S.C. 154(b) by 0 days.

(21) Appl. No.: 16/763,272

(22) PCT Filed: Sep. 12, 2018

(86) PCT No.: PCT/EP2018/074578
§ 371 (c)(1),
(2) Date: May 12, 2020

(87) PCT Pub. No.: WO2019/115032
PCT Pub. Date: Jun. 20, 2019

(65) Prior Publication Data
US 2020/0283319 A1    Sep. 10, 2020

(30) Foreign Application Priority Data

Dec. 12, 2017    (AT) ............................... A 51028/2017

(51) Int. Cl.
*C02F 9/00*       (2006.01)
*C02F 1/44*       (2006.01)
(Continued)

(52) U.S. Cl.
CPC ............... *C02F 9/00* (2013.01); *B01D 61/10* (2013.01); *B01D 61/58* (2013.01); *C02F 1/048* (2013.01);
(Continued)

(58) Field of Classification Search
CPC .... C02F 9/00; C02F 1/048; C02F 1/26; C02F 1/441; C02F 1/442; C02F 2001/5218;
(Continued)

(56) References Cited

U.S. PATENT DOCUMENTS 7,306,739 B1    12/2007  Camin et al.
9,926,613 B2 *   3/2018  Kishimoto ............... C13K 1/00
(Continued)

FOREIGN PATENT DOCUMENTS

| DE | 198 00 335 | 7/1999 |
| EP | 2 796 418 | 10/2014 |
| WO | 2010/037156 | 4/2010 |

OTHER PUBLICATIONS

Austria Search Report conducted in counterpart Austria Appln. No. A 51028/2017 (dated Aug. 31, 2018).
(Continued)

*Primary Examiner* — Joseph W Drodge
(74) *Attorney, Agent, or Firm* — Greenblum & Bernstein, P.L.C.

(57)    ABSTRACT

A process for the treatment of wastewater (S1) formed during the production of starches, in particular of chemically modified starches, and which contains dissolved salts and organic compounds, in which process it is proposed that the wastewater (S1) or pretreated wastewater (S1) containing substantially the dissolved salts and the organic compounds of the wastewater (S1) is subjected to a membrane separation process in which a separation of the wastewater (S1) supplied to the membrane separation process into a first volume flow (S3) with a higher concentration of dissolved salts in relation to the supplied wastewater (S1) and a second volume flow (S2) with a reduced concentration of dissolved salts in relation to the supplied wastewater (S1) is performed, wherein the first volume flow (S3) is subjected to thermal treatment for the separation of the dissolved salts and of a third volume flow (S9) which contains a fraction of the organic compounds of the wastewater (S1). By means of the invention, a process for the treatment of the wastewater
(Continued)

(S1) from the production of modified starches with recovery of utilizable contents is provided.

9 Claims, 1 Drawing Sheet

(51) Int. Cl.
| | |
|---|---|
| *C02F 1/26* | (2006.01) |
| *B01D 61/10* | (2006.01) |
| *B01D 61/58* | (2006.01) |
| *C07C 27/28* | (2006.01) |
| *C07C 27/34* | (2006.01) |
| *C02F 1/04* | (2006.01) |
| *C02F 1/52* | (2006.01) |
| *C02F 101/10* | (2006.01) |
| *C02F 101/32* | (2006.01) |
| *C02F 103/28* | (2006.01) |
| *C02F 103/32* | (2006.01) |
| *B01D 9/00* | (2006.01) |

(52) U.S. Cl.
CPC ............... *C02F 1/26* (2013.01); *C02F 1/441* (2013.01); *C02F 1/442* (2013.01); *C07C 27/28* (2013.01); *C07C 27/34* (2013.01); *B01D 2009/0086* (2013.01); *B01D 2311/2669* (2013.01); *B01D 2311/2673* (2013.01); *C02F 2001/5218* (2013.01); *C02F 2101/101* (2013.01); *C02F 2101/322* (2013.01); *C02F 2103/28* (2013.01); *C02F 2103/32* (2013.01)

(58) Field of Classification Search
CPC .......... C02F 2101/101; C02F 2101/322; C02F 2103/28; C02F 2103/32; C02F 1/04; C02F 2103/26; C02F 2101/32; C02F 1/44; C02F 2001/30; C02F 2001/32; C02F 2001/322; Y02W 10/40; B01D 3/00; B01D 3/001; B01D 3/14; B01D 3/143; B01D 3/145; B01D 3/146; B01D 3/148; B01D 1/26; B01D 9/00; B01D 9/004; B01D 9/0059; B01D 9/2009; B01D 9/0086; B01D 9/009; B01D 11/04; B01D 11/0488; B01D 11/0492; B01D 61/02; B01D 61/022; B01D 61/025; B01D 61/027; B01D 61/10; B01D 61/58; B01D 2221/10; B01D 2311/04; B01D 2311/06; B01D 2311/08; B01D 2311/26; B01D 2311/2669; B01D 2311/2673; C07C 27/26; C07C 27/28; C07C 27/32; C07C 27/34; C07C 29/76; C07C 29/78; C07C 29/80; C07C 29/84; C07C 29/86; C08L 3/00; C08L 3/02; C08L 3/04; C08B 30/00; C08B 30/02; C08B 30/04; C08B 30/08; C08B 31/00; C08B 31/18
See application file for complete search history.

(56) References Cited

U.S. PATENT DOCUMENTS

| | | | | |
|---|---|---|---|---|
| 2002/0030016 | A1* | 3/2002 | Schmidt | B01D 61/16 210/650 |
| 2009/0008235 | A1* | 1/2009 | Goel | B01D 3/002 203/41 |
| 2011/0250637 | A1* | 10/2011 | Kurihara | B01D 61/025 435/41 |
| 2012/0178976 | A1* | 7/2012 | Hennessey | C12P 1/00 568/913 |
| 2012/0253082 | A1* | 10/2012 | Morita | C07C 29/76 568/869 |
| 2012/0321871 | A1* | 12/2012 | Bond | C08K 11/00 428/220 |
| 2013/0079509 | A1* | 3/2013 | Mattila | B01D 65/06 536/127 |
| 2013/0158169 | A1* | 6/2013 | Bond | C08L 23/12 524/51 |
| 2013/0266991 | A1* | 10/2013 | Kanamori | C12P 19/14 435/99 |
| 2014/0017729 | A1* | 1/2014 | Minamino | C13K 13/007 435/85 |
| 2015/0083118 | A1* | 3/2015 | Kishimoto | B01D 61/022 127/55 |
| 2015/0122743 | A1* | 5/2015 | Theodore | C02F 1/70 210/719 |
| 2015/0259269 | A1* | 9/2015 | Lindstaedt | C07C 29/76 568/868 |
| 2016/0221851 | A1 | 8/2016 | Gonzalez | |
| 2017/0081426 | A1* | 3/2017 | Larry | B01D 21/2427 |
| 2018/0311618 | A1* | 11/2018 | Benton | C12H 3/04 |

OTHER PUBLICATIONS

Int'l Search Report (Form PCT/ISA/210) conduced in Int'l Appln. No. PCT/EP2018/074578 (dated Oct. 16, 2018).
Int'l Written Opinion (Form PCT/ISA/237) conduced in Int'l Appln. No. PCT/EP2018/074578 (dated Oct. 16, 2018).

* cited by examiner

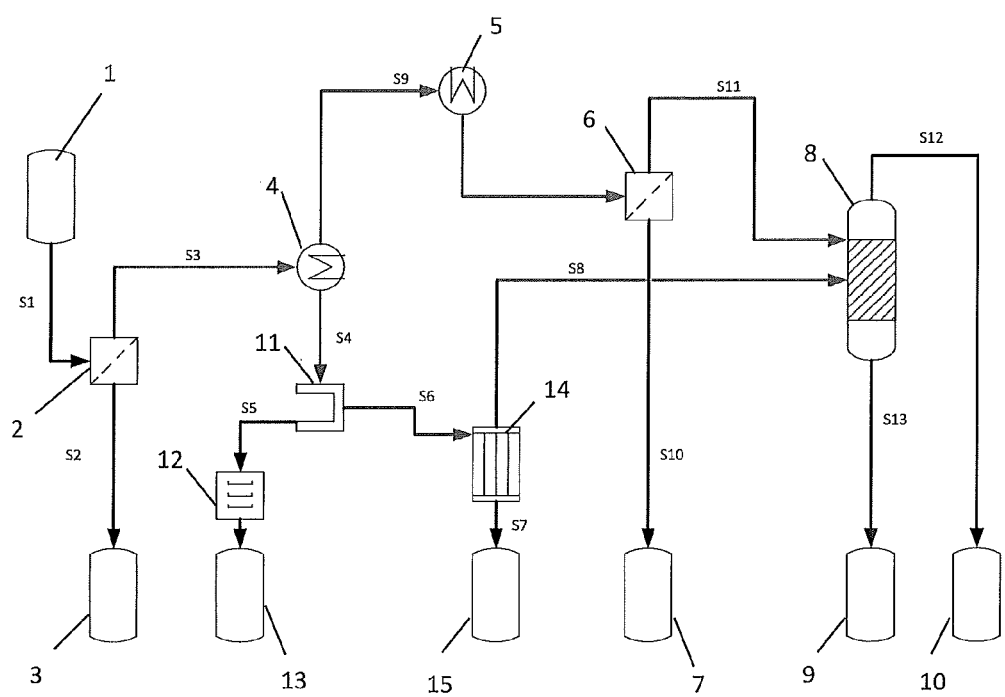

PROCESS FOR THE TREATMENT OF WASTEWATER FORMED DURING THE PRODUCTION OF MODIFIED STARCHES

The invention relates to a process for the treatment of wastewater produced during the production of starches, in particular chemically modified starches, and containing dissolved salts and organic compounds, according to the preamble of claim 1.

Modified starches have a wide range of applications in industry, with the main areas of application being in the food and paper industries. They can be produced physically, chemically or enzymatically. In the case of chemically modified starches, the properties of the starch are adapted to the respective requirements by the use of chemicals. This makes it possible, for example, to change the physical and rheological properties as well as the swelling and water-binding properties of the starch. Starch can be obtained from raw materials such as corn, wheat, potato, tapioca or rice. The chemical modification is carried out in aqueous solution or suspension by adding chemicals to the starch suspended in water ("slurry"). The wastewater to be purified according to the invention results from the separation and washing out of the modified starch from the reaction mixture. Washing is usually carried out by a hydro-washing cyclone plant and the starch is usually separated by centrifugal separators such as separators and/or centrifuges.

The wastewater remaining after separation and leaching of the modified starch contains high concentrations of organic compounds and dissolved salts. In the production of hydroxypropyl starch (HPS), for example, wastewater with high concentrations of 1,2-propanediol and sodium sulfate is produced. Traditionally, this wastewater is treated in biological wastewater treatment plants, wherein the organic compounds are broken down by aerobic processes and converted into biomass ("sludge"). However, the high fraction of dissolved salts causes great difficulties in this biological wastewater treatment. With increasing salt concentration, the biocenosis in the biological wastewater treatment is inhibited, which can lead to functional disturbances up to the complete cessation of the biological wastewater treatment. The high sulphate concentration in the wastewater additionally leads to corrosion in the plant technology and in the concrete basins of the wastewater treatment plants. The salt load is not decomposed in the biological wastewater treatment plant and therefore reaches the receiving water via the outlet and pollutes it. In addition, the biomass ("sewage sludge") produced in the biological wastewater treatment stage usually has to be disposed of at great expense.

Further processes for the treatment of wastewater from the production of modified starches were described in EP 2796418 A1 and WO 2010/037156 A1. Processes for the treatment of wastewater from the processing of potatoes were described in U.S. Pat. No. 7,306,739 B1 and DE 198 00 335 A1.

It is thus the object of the invention to improve the treatment of the wastewater resulting from the production of starches, in particular chemically modified starches, and in particular to provide a process for treating the wastewater while recovering usable ingredients.

These objects are achieved by the features of claim 1. Claim 1 relates to a process for the treatment of wastewater resulting from the production of starches, in particular chemically modified starches, and containing dissolved salts and organic compounds, in which it is proposed according to the invention that the wastewater or a pre-treated wastewater substantially containing the dissolved salts and organic compounds of the wastewater is subjected to a membrane separation process, in which the wastewater fed to the membrane separation process is separated into a first volume flow with a higher concentration of dissolved salts compared with the supplied wastewater and into a second volume flow with a lower concentration of dissolved salts compared with the supplied wastewater, wherein the first volume flow is subjected to a thermal treatment to separate the dissolved salts and a third volume flow containing a fraction of the organic compounds of the wastewater, and the third volume flow or a volume flow derived therefrom is subjected to a selective fractionation for the separation and recovery of 1,2-propanediol or ethylene glycol. According to the invention, a separation of the wastewater into different volume flows is thus carried out, wherein the dissolved salts are concentrated in a first volume flow, and at least a fraction of the organic compounds is concentrated in a third volume flow. At least the fraction of the organic compounds contained in the third volume flow is subsequently available for recovery, as will be explained in more detail below. The dissolved salts are recovered by thermal treatment of the first volume flow, wherein recovery by thermal treatment is economically feasible because the first volume flow has a significantly smaller volume than the wastewater originally supplied to the membrane separation process. In fact, the process according to the invention proves to be economically viable solely by recovery and reuse of the recovered salts despite the energy required for the thermal treatment. If the organic compounds 1,2-propanediol or ethylene glycol contained in the third volume flow are also recovered and recycled, the economic balance of the process according to the invention is clearly positive. Optionally, the wastewater resulting from the production of starches, in particular chemically modified starches, can be subjected to a pretreatment to separate suspended solids before it is supplied to the membrane separation process provided according to the invention.

Preferably, reverse osmosis is carried out in the membrane separation process, wherein the first volume flow contains not only the higher concentration of dissolved salts compared to the supplied wastewater, but also the organic compounds of the supplied wastewater. In this case, the second volume flow represents water substantially freed from dissolved salts and organic compounds, which can be reused in the production process of starch or modified starch and allows a significant reduction of the volume of the first volume flow to be treated. Thus, the first volume flow can be directly fed in an economically justifiable way to the thermal treatment for the recovery of the salts.

Alternatively, nanofiltration can also be carried out in the membrane separation process, wherein the second volume flow contains a reduced concentration of dissolved salts compared to the supplied wastewater, as well as a further fraction of organic compounds. This embodiment can be advantageous, for example, if a part of the organic compounds is to be used in a biogas plant, for example, in order to generate the energy required for the thermal treatment to separate and recover the dissolved salts, thus making the overall process more economical.

According to an advantageous embodiment, the thermal treatment of the first volume flow is carried out in a crystallization plant under crystallization of dissolved salts.

According to the invention, the third volume flow or a volume flow derived from it undergoes selective fractionation for the separation and recovery of 1,2-propanediol or ethylene glycol. The recovered organic compounds 1,2-propanediol or ethylene glycol represent an economically viable raw material. Preferably, the selective fractionation for the separation and recovery of the organic compounds is a distillation or extraction. Alternatively, however, the use of rectification, adsorption or absorption for the selective fractionation of the organic compounds would also be conceivable.

It is preferably proposed that the third volume flow is liquefied and subjected to reverse osmosis to separate water before selective fractionation to separate and recover the 1,2-propanediol or ethylene glycol. In this way, the volume flow supplied to selective fractionation can be reduced. Selective fractionation can thus be dimensioned smaller and more cost-effectively and energy consumption can be reduced.

In order to increase the quantities of both recovered salts and organic compounds, it is further proposed that the mother liquor of the crystallization plant is evaporated and the evaporator vapor resulting from the evaporation of the mother liquor is sent to selective fractionation for the separation and recovery of the organic compounds 1,2-propanediol or ethylene glycol contained in the mother liquor. The dry residues of the mother liquor are formed by the now recovered and reusable salts, and the evaporator vapor contains usable volatile organic compounds which are recovered by the selective fractionation.

If nanofiltration is carried out as a membrane separation process in accordance with the invention, the second volume flow can be subjected to reverse osmosis and the retentate of the reverse osmosis can be supplied to the selective fractionation for the separation and recovery of the organic compounds 1,2-propanediol or ethylene glycol contained in the retentate. For the separation of the non-volatile components contained in the second volume flow, it is advantageous to evaporate the retentate before supplying it to the selective fractionation, wherein the evaporator vapor resulting from the evaporation of the retentate is also supplied to the selective fractionation for the separation and recovery of the organic compounds. The evaporation of the mother liquor of the crystallization plant and the retentate can take place approximately together in a thin-film evaporator.

The invention will be explained in more detail below by means of an embodiment example using the enclosed figures, wherein:

FIG. 1 shows a schematic representation of a possible embodiment of the process according to the invention.

As can be seen in FIG. 1, the wastewater S1 remaining after separation and washing out of the modified starch is first kept in a wastewater tank 1. The wastewater S1 contains high concentrations of organic compounds and dissolved salts. During the production of hydroxypropyl starch (HPS), for example, wastewater S1 with high concentrations of 1,2-propanediol and sodium sulphate or other salts such as ammonium sulphate is produced. For the separation of suspended solids, the wastewater S1 can, if necessary, be supplied to a pre-treatment stage (not shown in FIG. 1), for example a filtration stage, before it is supplied to a first membrane stage 2, in which a membrane separation process is carried out, in the example shown in FIG. 1 in the form of reverse osmosis.

In the first membrane stage 2, the wastewater S1 supplied to the first membrane stage 2 is separated into a first volume flow S3 with a higher concentration of dissolved salts compared to the supplied wastewater S1 and into a second volume flow S2 substantially freed from dissolved salts. When reverse osmosis is used, the organic compounds are also in the first volume flow S3. The second volume flow S2 is thus water substantially freed from dissolved salts and organic compounds, which can be collected in a first water tank 3 and reused in the production process of starch or modified starch, or elsewhere in the plant. Due to the separation of the second volume flow S2, the first volume flow S3 thus has a significantly reduced volume compared to the wastewater S1 supplied to the first membrane stage 2. Thus, the first volume flow S3 can be supplied in an economically viable way directly to a crystallization plant 4 for the thermal treatment of the first volume flow S3 and recovery of the dissolved salts.

In crystallization plant 4, the first volume flow S3 is evaporated with crystallization of the dissolved salts. The vapor produced in crystallization plant 4 contains hardly any dissolved salts but a high concentration of volatile organic compounds and represents a third volume flow S9, which is first liquefied in a condenser 5. The heat to be dissipated can be used for thermal treatment or for the subsequent distillation by means of heat recovery (not shown in FIG. 1). The liquefied third volume flow S9 is then fed to a second membrane stage 6 according to the embodiment example in FIG. 1, where it is subjected to reverse osmosis. In the second membrane stage 6, a first purified water fraction S10 is obtained, which is collected in a second water tank 7 and can be reused in the production process of starch or modified starch, or also at another point of the operation.

From the second membrane stage 6, a highly concentrated fraction of organic compounds, S11, can also be derived, which is then subjected to selective fractionation for the separation and recovery of the organic compounds. In the embodiment example shown in FIG. 1, the selective fractionation is carried out in a distillation plant 8, wherein the desired organic compounds can be selectively recovered as organic fraction S13 and collected in a collection tank 9. In the production of hydroxypropyl starch (HPS), for example, wastewater S1 with a high concentration of 1,2-propanediol is produced, which can be recovered as organic fraction S13 by means of the process shown in FIG. 1 in distillation plant 8, stored in collection tank 9 and subsequently economically utilized. The organic fraction S13 is preferably cooled, wherein the heat to be dissipated can be used, for example, for heating up distillation plant 8 or for the thermal treatment of supplied media. A final volume flow S12 of distillation plant 8 represents a second purified water fraction S12, which can be collected in a third water tank 10 and reused in the production process of starch and modified starch. The purified water fraction S12 is also preferably cooled, wherein the waste heat can be used in the process for heating media.

The residue S4 of crystallization plant 4 is first supplied to a centrifuge 11, in which the crystallized salts are separated as the first salt fraction S5 and dried in a dryer 12. The dried salt is collected in a first salt silo 13. In the production of hydroxypropyl starch (HPS), for example, wastewater S1 with a high concentration of sodium sulfate is produced, which is collected in the first salt silo 13 and can be reused in the production process of the modified starch.

The mother liquor S6 leaving centrifuge 11 and crystallization plant 4 contains a high concentration of salts, non-evaporable residues and volatile organic compounds. It is fed to a thin-film evaporator 14 to recover the contained salts as a second salt fraction S7, which can be collected in a second salt silo 15. The evaporator vapor S8 of the thin film evaporator 14 contains water and volatile organic compounds and is supplied to distillation plant 8 to achieve almost complete recovery of these organic compounds.

In fact, the process according to the invention proves to be economically viable simply by recovering and recycling the recovered salts, despite the energy required for thermal treatment in crystallization plant 4. Due to the additional recovery and recycling of the organic compounds, the economic balance of the process according to the invention is clearly positive. In addition, the recovery of water and dissolved salts, which can be reused as recovered raw materials in the production process of the modified starch, reduces the raw material costs for the manufacturing process and almost completely eliminates the considerable consumption of drinking water and the quantities of wastewater to be discharged in the production of chemically modified starches. When planning a new plant for the production of modified starches, it is possible to dispense with biological wastewater treatment and thus avoid the disposal of the biomass (sewage sludge) produced therein. In existing plants, the hydraulic and organic load of the biological wastewater treatment plant can be reduced with the help of the process according to the invention, thus creating wastewater treatment reserves.

The invention claimed is:

1. Process for the treatment of wastewater obtained in the production of starch, optionally including chemically modified starch, and containing dissolved salts and organic compounds, said process comprising:
   subjecting the wastewater, optionally being pretreated, containing the dissolved salts and the organic compounds to a membrane separation process in which a separation of the wastewater supplied to the membrane separation process into a first volume flow with a higher concentration of dissolved salts in comparison with the supplied wastewater and into a second volume flow with a lower concentration of dissolved salts in comparison with the supplied wastewater is carried out;
   wherein the first volume flow is subjected to a thermal treatment for separating the dissolved salts and a third volume flow containing a fraction of the organic compounds of the wastewater, and the third volume flow or a volume flow derived therefrom is subjected to a selective fractionation for separation and recovery of 1,2-propanediol or ethylene glycol.

2. Process according to claim 1, further comprising:
   carrying out a reverse osmosis in the membrane separation process, wherein the second volume flow is water substantially freed from dissolved salts and organic compounds.

3. Process according to claim 1, further comprising:
   carrying out a nanofiltration in the membrane separation process, wherein the second volume flow represents a volume flow containing a further fraction of the organic compounds of the wastewater.

4. Process according to claim 3, further comprising:
   subjecting the second volume flow to reverse osmosis; and
   supplying a retentate of the reverse osmosis to the selective fractionation for separating and recovering the organic compounds contained in the retentate.

5. Process according to claim 1, further comprising:
   carrying out the thermal treatment of the first volume flow in a crystallization plant with crystallization of dissolved salts.

6. Process according to claim 5, further comprising:
   evaporating a mother liquor of the crystallization plant; and
   supplying the evaporator vapor resulting from the evaporation of the mother liquor to the selective fractionation for the separation and recovery of 1,2-propanediol or ethylene glycol contained in the mother liquor.

7. Process according to claim 1, wherein:
   the selective fractionation is a distillation.

8. Process according to claim 1, wherein:
   the selective fractionation is an extraction.

9. Process according to claim 1, further comprising:
   before the selective fractionation for the separation and recovery of 1,2-propanediol or ethylene glycol, liquefying and subjecting the third volume flow to reverse osmosis for the separation of water.

* * * * *